United States Patent

Prasad

Patent Number: 4,970,320
Date of Patent: Nov. 13, 1990

[54] PREPARATION OF PHENOXY-TRIAZOLYL-PINACOL-ONES

[75] Inventor: Vidyanatha A. Prasad, Leawood, Kans.

[73] Assignee: Mobay Corporation, Pittsburgh, Pa.

[21] Appl. No.: 469,615

[22] Filed: Jan. 24, 1990

[51] Int. Cl.$^5$ .......................................... C07D 249/08
[52] U.S. Cl. ................................................ 548/268.2
[58] Field of Search ..................................... 548/268.2

[56] References Cited

U.S. PATENT DOCUMENTS 3,912,752  10/1975  Meiser et al. ............... 548/268.2

OTHER PUBLICATIONS

Kulesar et al., "Preparation of 1-Azolyl, etc." CA 111:97245f (1984).

Primary Examiner—Glennon H. Hollrah
Assistant Examiner—Patricia L. Morris
Attorney, Agent, or Firm—Joseph C. Gil; Lyndanne M. Whalen

[57] ABSTRACT

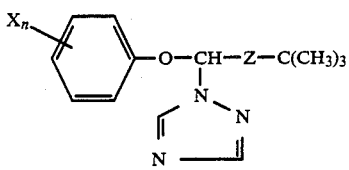

in which
Z represents —CO—,
X represents a halogen, phenyl, phenoxy or halo-phenoxy moiety, and
n is an integer of from 0 to 5,
is produced by reacting 1,2,4-triazole with an α-halo-α-phenoxy compound of the formula

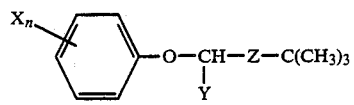

in which Y represents Br or Cl,
in the presence of a tertiary amine and a water-immiscible organic solvent. The amine is liquid at ambient temperature, substantially water-insoluble in its free base form and water-soluble in salt form.

18 Claims, No Drawings

PREPARATION OF PHENOXY-TRIAZOLYL-PINACOL-ONES

BACKGROUND OF THE INVENTION

The present invention relates to a process for the preparation of phenoxy-triazolyl-pinacol-ones which are known to be useful as fungicides and anti-mycotics.

U.S. Pat. No. 3,912,752 discloses the preparation of fungicides corresponding to the formula

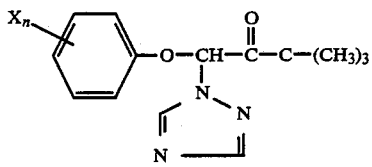

by several different processes, one of which comprises reacting

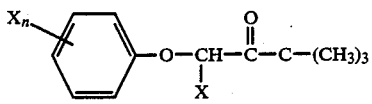

in which X represents halogen and n is from 1 to 5, with 1,2,4-triazole in a solvent.

Although this synthesis is feasible, there are certain features which significantly affect the cost of producing such fungicides. Specifically, the process taught in U.S. Pat. No. 3,912,752 requires an excess of at least 100% of the expensive triazole. The excess serves as an acid acceptor to carry the reaction forward and to completion. Recovery of the excess triazole on an industrial scale is difficult because the triazole is completely miscible with water and fairly insoluble in most organic solvents which may be used as process solvents, e.g., toluene. Accordingly, some of the expensive triazole is lost in conventional recovery processes. Recovery also poses problems because the recycled triazole is a solid mixed with inorganic salt so that purification of the triazole is necessary before it can be re-used. Triazole losses in the recovery step result in organic waste in process water which water must then be treated at considerable expense.

SUMMARY OF THE INVENTION

It is an object of the present invention to provide a process for reacting an azole with an α-halo-α-phenoxy-pinacol-one under conditions such that the expensive recovery process for triazole is unnecessary and loss of triazole is minimized.

It is also an object of the present invention to provide a process for reacting an azole with an α-halo-α-phenoxy-pinacol-one in the presence of a tertiary amine which is normally liquid at ambient temperature, insoluble in water in its free base form but soluble in water when in salt form. This amine is advantageously used in a quantity such that it will produce sufficient free azole for further reaction thereby eliminating the need for substantial excess quantities of azole being initially present in the reaction mixture and simplifying product recovery processes.

These and other objects, which will be apparent to those skilled in the art, are accomplished by reacting 1,2,4-triazole with an α-halo-α-phenoxy-compound of the formula

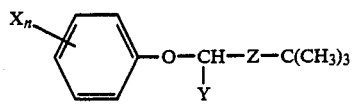

in which
Y represents Br or Cl and
Z represents —CO—
in an organic solvent to form

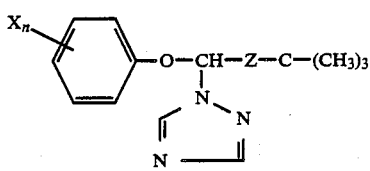

in which
Z represents —CO—,
X represents a halogen, phenyl, phenoxy or halophenoxy moiety, and
n is an integer of from 0 to 5.

In the process of the present invention, a portion of the phenoxy compound is mixed with substantially all of the required amount of 1,2,4-triazole. The initial portion of the phenoxy compound should be sufficient to produce triazole hydrohalide, preferably triazole hydrochloride. Thereafter the reaction mass is heated. During the course of the resultant reaction, a portion of tertiary amine which is normally liquid at ambient temperature is added in an amount sufficient to produce free triazole for subsequent reaction without side reactions. The tertiary amine is substantially water-insoluble in its free base form, but water-soluble in salt form. The remainder of the required amount of the tertiary amine and the remainder of the required amount of the phenoxy compound are then added alternately in one or more portions. Upon termination of the reaction, the reaction mass is washed with water under acid conditions to extract the tertiary amine salt into the water. The desired product remains in the substantially tertiary amine-free organic solvent.

DETAILED DESCRIPTION OF THE INVENTION

Compounds corresponding to formula II are produced by reacting a phenoxy compound corresponding to formula I with triazole in the presence of a tertiary amine and a water immiscible solvent. In the process of the present invention, a portion of the phenoxy compound corresponding to formula I is mixed with substantially all of the required amount of triazole. The amount of this phenoxy compound portion should be sufficient to produce triazole hydrohalide, preferably triazole hydrochloride. After heating this mixture, a portion of a tertiary amine which is normally liquid at ambient temperature is added. The amount of tertiary amine added should be sufficient to produce free triazole without causing unwanted side reactions. The tertiary amine is substantially water insoluble in its free base form but should be water soluble when in the form of its salt. The remaining portions of phenoxy compound and of tertiary amine are then added. Upon termination of the reaction, the reaction mass is treated with water under acidic conditions to extract tertiary amine salt and leave the desired product in the substantially tertiary amine-free organic solvent.

In a preferred embodiment, the initial portion of the phenoxy compound is mixed with about twice its molar amount of the 1,2,4-triazole (i.e., the triazole is preferably added along with approximately half the total required amount of the phenoxy compound). The initial portion of the liquid tertiary amine is added in an amount which is approximately equal to the amount of the initial portion of phenoxy compound. In a particularly preferred embodiment, the two portions of the phenoxy compound are approximately equal.

In another embodiment of the present invention, the initial portion of the phenoxy compound is mixed with substantially all of the required amount of the 1,2,4-triazole. The amount of this initial portion of the phenoxy compound should be sufficient to produce triazole hydrohalide. The resultant mixture is then heated. During the course of the resultant reaction, an initial portion of a tertiary amine which is normally liquid at ambient temperature is added in a quantity sufficient to produce free triazole for subsequent reaction without side reactions. The amine used should be substantially water-insoluble in its free base form but water-soluble in salt form. Thereafter, at least two portions of each of the remaining amounts of the total required amounts of the phenoxy compound and the amine are added alternately. This alternate addition is carried out in a manner such that (i) a portion of one of the remainder of the phenoxy or the amine is added, (ii) the reaction mixture is then maintained at reaction temperature for a period of from about one minute to about one-half hour, preferably from about 2 minutes to about 10 minutes and most preferably for about 5 minutes, (iii) a portion of the other of the remainder of the phenoxy compound or amine is then added, and (iv) the reaction mixture is again maintained at reaction temperature for a period within the time range described in (ii). Steps (i) to (iv) are repeated until the remaining amounts of the phenoxy compound and the amine are consumed. At the end of the reaction, the reaction mass is washed with water under acidic conditions to extract the tertiary amine salt into the water, while leaving the desired product in substantially tertiary amine-free organic solvent. It is preferred that the remainder of the phenoxy compound and the tertiary amine each be about one-half of the required amount and that each is alternately added. This preferred embodiment of the invention may be summarized as follows:

I. Initially, one half of the total required amount of phenoxy compound and one half of the total required amount of amine are mixed. Substantially all of the required amount of triazole is included in this mixture.

II. Alternate additions of the remaining portion(s) of phenoxy compound and the remaining portion(s) of amine to be used may be made in accordance with the steps outlined in the following procedure.

STEP IIA
(i) One third of the remaining half of the total required amount of phenoxy compound is added.
(ii) The reaction mixture is maintained at reaction temperature for from about 1 minute to about 30 minutes.
(iii) One third of the remaining one half of the total required amount of the amine is added.
(iv) The reaction mixture is maintained at reaction temperature for from about 1 minute to about 30 minutes.

STEP IIB
(i) A second third of the one half of the total required amount of the phenoxy compound not mixed in I is added.
(ii) The mixture is maintained at reaction temperature for from about 1 minute to about 30 minutes.
(iii) A second third of the one half of the total required amount of the amine not mixed in I is added.
(iv) The mixture is maintained at reaction temperature for from about 1 minute to about 30 minutes.

STEP IIC
(i) The last third of the one half of the total required amount of the phenoxy compound which was not added in I is added.
(ii) The mixture is maintained at reaction for from about 1 minute to about 30 minutes.
(iii) The last third of the one half of the total required amount of the amine which was not added in I is added.
(iv) The mixture is maintained at reaction temperature for from about 1 minute to about 30 minutes.

Upon termination of the reaction, substantially all of the tertiary amine is present as its hydrohalide salt. The salt enters the aqueous phase during the water wash. The resultant aqueous and organic phases separate cleanly. After separation of the aqueous and organic phases, an alkali material is added to the separated aqueous phase. The tertiary amine is set free from its salt. The free amine may be recovered by extraction in the residual organic solvent (e.g., toluene) and then recycled. A small amount of fresh tertiary amine may be added to the organic solvent to make up for small losses. The waste water layer is substantially free of organic material which organic material would be a pollutant if discharged.

Alternatively, the regenerated free tertiary amine in toluene can be subjected to steam distillation to recover purified tertiary amine for recycle.

The principal reaction, i.e. reaction of triazole with halophenoxy compound proceeds stoichiometrically and substantially fully in the process of the present invention. The desired product remains in the organic phase after mixing the reaction mass with water. The organic phase may be distilled to remove the organic solvent for re-use, leaving behind the desired product which can then be dried and formulated in known manner.

In accordance with preferred features of the invention, X and halogen in the formulae are each chlorine. Approximately equimolar amounts of the 1,2,4-triazole, the $\alpha$-halo-$\alpha$-phenoxy compound and the liquid tertiary amine are employed, although an excess of the triazole may be used.

The tertiary amine is advantageously a substantially water-insoluble substituted pyridine, e.g. 2,4-dimethylpyridine, preferably it is an amine corresponding to the formula $NR_1R_2R_3$ in which $R_1$, $R_2$ and $R_3$ each represents an alkyl group of up to 16 carbons (preferably an alkyl group of up to 4 carbon atoms), or an aryl group with up to 16 carbon atoms (such as a phenyl group), or an aralkyl group with up to 16 carbon atoms (preferably, benzyl or phenethyl).

As noted, the tertiary amines should be substantially water-insoluble in free base form, e.g. less than 0.2% soluble at room temperature, but in salt form should dissolve to at least 20 to 40%. A highly water-soluble amine such as triethylamine works in the initial reaction but is difficult to recover and recycle thus posing pollution problems. Similarly, inorganic bases such as sodium hydroxide and potassium carbonate do not give results comparable to those achieved by the tertiary amines meeting the solubility requirements described above.

The organic solvent in which the reaction of the present invention is carried out is preferably toluene but xylenes and halogenated aliphatic and aromatic hydrocarbons of suitable boiling point can also be used. Specific examples of such solvents are given in U.S. Pat. No. 3,912,752, supra.

The reactants are preferably used in stoichiometric amounts although either could be used in excess. Use of an excess would, however, be wasteful because the reaction proceeds to completion at a good rate when stoichiometric amounts are employed.

A very important feature of the invention is the slow addition of tertiary amine after the initial reaction, with the balance of the phenoxy compound being added after the addition of the tertiary amine has begun. If all of the tertiary amine were present from the outset of reaction, there would be a tendency for it to enter into a side reaction with the phenoxy compound, thereby reducing the yield and complicating recovery. When all of the amine is added at the end of the reaction, the reaction proceeds much more slowly.

By slow addition is meant the approximate rate of consumption. Since the reaction generally takes a few hours, a rate which has been found to be particularly advantageous is a rate of less than about 2% and preferably less than about 1% per minute, based on the total or stoichiometric amount of tertiary amine added.

The reaction which takes place during the process of the present invention, proceeds in conventional manner at elevated temperature, e.g. 50° to 150° C., with pressure if desired and/or needed to keep the solvent from boiling off.

Advantageously, all of the triazole and half of the chloropinacolone are reacted first, similar to the conventional process, using at least a 100% excess of the triazole, to produce the product and triazole hydrochloride. Then, the addition of the tertiary amine is begun; the tertiary amine reacts with the triazole hydrochloride to release free triazole and is itself quaternized. When sufficient free triazole has been produced, the addition of the other half of the chloropinacolone is started. At this point, the two additions, i.e., of the tertiary amine and chloropinacolone, are simultaneous additions.

This approach essentially constitutes an "in situ triazole recovery".

The invention will be further described in the following illustrative non-limiting examples in which all parts are by weight unless otherwise indicated.

EXAMPLES

EXAMPLE 1

A 4-necked round bottom flask was fitted with an overhead stirrer, thermometer, condenser, addition funnels and heating mantle. 80.0 g (1.1M) of triazole were charged to the flask along with a minimum amount of toluene. The triazole was dried azeotropically. 259.75 g of a 52% solution of 4-chloro-4-(4-chlorophenoxy)-2,2-dimethyl-butan-3-one (0.5M) in toluene were added all at once to the toluene triazole slurry at 35° to 40° C. The mixture was heated to 87° C. with agitation in ten minutes, and held at 87° to 90° C. for 1 hour in order to generate sufficient triazole hydrochloride. Then, addition of N,N-dimethyl-benzylamine was started and the add-rate was adjusted so that 128.5 g of the N-dimethyl-benzylamine were added in two hours. Forty-five minutes after the beginning of the N,N-dimethyl-benzylamine addition, addition of another 259.75 g (0.5 M) of the toluene butanone solution was commenced. The addition rate was adjusted so that 259.75 g of solution were added in one hour and fifteen minutes, i.e., the two separate additions were completed at the same time. The entire mixture was cooked for one hour at 87° to 90° C. to complete the reaction. If the reaction had not been completed at this point (which may be readily determined by GC analysis), enough triazole (but no amine) could be added based on the amount of unreacted butanone and the mixture cooked to completion.

At the end of the reaction, no free amine was detected by G.C. analysis, all having been converted to the hydrochloride. The entire mixture was cooled to 25° to 30° C. and drowned with 125 g of water with agitation to dissolve the solids. The pH of the system was 2.0. The layers were separated. The aqueous layer was retained for amine recovery. The organic layer was washed with 50 g of 15% HCl (pH 0.5). The entire mixture was filtered and the layers were separated (filtration may sometimes be necessary to remove tarry materials, if present). The aqueous layer was combined with the previously obtained aqueous layer and retained for amine recovery. The organic layer was treated with 125 g of water and enough 50% NaOH to attain a pH of 12.0. The entire mixture was filtered and the layers were separated. The aqueous layer was discarded. The organic layer was checked to see if it was free of amine and p-chlorophenol (if amine had appeared after the caustic wash step, another acid wash could have been undertaken in order to remove it and realize optimum AI's and high amine recoveries). The organic layer (solution of active material in toluene) was steam stripped and there were obtained 284 g of dry crude 4-(4-chloro-phenoxy)-2,2-dimethyl-4-(1,2,4-triazol-1-yl)-butan-2-one, i.e., 96.7% crude yield 1.0M of starting butanone.

A.I. by HPLC: 94.2%
Net Yield (based on butanone): 91.1%

EXAMPLE 2

The materials used in this procedure were as follows: 66.6 g (0.25 moles) of 4-chloro-4-(4-chlorophenoxy 2,2-dimethyl-butan-3-one (assumed 98% purity) 81 g of toluene (to make an approximate 45% chloropinacoline solution in toluene) 20.9 g of triazole (i.e., 0.25 moles + 15% excess (purity 95%)) 28.7 g (0.21 moles, i.e., 15% deficiency) of N,N-dimethylbenzylamine diluted with 15 g of toluene.

Procedure: A 500 ml 4-necked round bottom flask was fitted with an overhead stirrer, thermometer, condenser, addition funnels and heating mantle. 20.9 g (0.25 moles + 15% excess) of triazole were charged to the flask along with a minimum amount of toluene. The triazole was dried azeotropically. The flask was fitted with a thermometer, a condenser, a 125 ml barostatic addition funnel containing 28.7 g (0.21M, i.e., 15% deficiency) of N,N-dimethylbenzylamine dissolved in 15 g of toluene and a 250 ml barostatic addition funnel containing a solution of 66.6 g of 4-chloro-4-(4-chlorophenoxy)-2,2-di-methyl-butan-3-one in 81 g of toluene. 50% of the chloropinacolone-toluene solution was added over a period of one hour at a uniform rate. The mixture was heated at 85° to 90° C. for one hour in order to generate sufficient triazole hydrochloride. The addition of the N,N-dimethylbenzylamine dissolved in toluene was begun. 50% of it was added over a 45 minute period at a uniform rate. During such addition a temperature of 85° to 90° C. was maintained. The mixture was heated for 5 minutes at this temperature. The addition of the 4-chloro-4-(4-chlorophenoxy)-2,2-dimethyl-butan-3-one and toluene solution was begun again. One-third (33%) of the remainder of the 4-chloro-4-(4-chlorophenoxy)-2,2-dimethyl-butan-3-one and toluene solution was added over a 15 minute period at a uniform rate at 80° to 9° C. The mixture was heated for 5 minutes at this temperature. The addition of the N,N-dimethylbenzyl-amine-toluene solution was begun again. One-third (33%) of the remainder of the N,N-dimethylbenzyl-amine-toluene solution was added over a 15 minute period at a uniform rate at 85° to 90° C. The mixture was heated for 5 minutes at this temperature. The addition of the second one-third portion of the 4-chloro-4-(4-chlorophenoxy)-2,2-di-methyl-butan-3-one and toluene solution was resumed for 15 minutes at a uniform rate at 85° to 9° C. The mixture was heated at 85° to 90° C. for 5 minutes. The addition of the second one-third portion of the N,N-dimethylbenzylamine-toluene solution was resumed for 15 minutes at a uniform rate at 85° to 90° C. The mixture was maintained at 85° to 90° C. for 5 minutes. The addition of the final one-third portion of the 4-chloro-4-(4-chlorophenoxy)-2,2-dimethyl-butan-3-one and toluene solution over a period of 15 minutes was begun at a uniform rate at 85° to 90° C. The mixture was heated at 85° to 90° C. for 5 minutes. The addition of the last one-third portion of the N,N-dimethylbenzylamine-toluene solution over 15 minutes was begun at a uniform rate at 85° to 90° C. The resultant mixture was heated for one hour at 85° to 90° C. Analysis showed that less than 0.1% 4-chloro-4-(chlorophenoxy)-2,2-dimethyl-butan-3-one remained.

Crude yield of product: 95.6%
Purity: 97.6%
Net yield: 93.3%

During this procedure, 4-chloro-4-(chlorophenoxy),2,2-dimethyl-butan-3-one and N,N-dimethybenzylamine were not added simultaneously. They were added alternately, in portions, at uniform rates of addition. The advantage of this approach is that at any given instant, no free chloropinacolone is exposed to attack by the N,N-dimethylbenzylamine. The N,N-dimethylbenzylamine simply enters the system and releases triazole from its hydrochloride each time. A series of in situ triazole recovery recycles occur. More 4-chloro-4-(4-chloro-phenoxy)-2,2-dimethyl-butan-3-one then enters the system to react with the free triazole and so on.

It will be understood that the specification and examples are illustrative but not limitative of the present invention and that other embodiments within the spirit and scope of the invention will suggest themselves to those skilled in the art.

What is claimed is:
1. A process for the production of

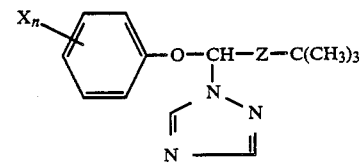

in which
Z represents —CO—,
X represents a halogen, phenyl, phenoxy or halophenoxy moiety, and
n is an integer of from 0 to 5,
in which 1,2,4-triazole is reacted with an α-halo-α-phenoxy compound of the formula

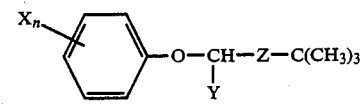

in which Y represents Br or Cl,
in the presence of a tertiary amine and a water-immiscible organic solvent by
(a) mixing an initial portion of the phenoxy compound with substantially all of the required amount of 1,2,4-triazole, said initial portion of the phenoxy compound being part of the total required amount of the phenoxy compound and being sufficient to produce triazole hydrohalide,
(b) heating the mixture of (a) to initiate reaction,
(c) adding to the resultant reaction mass during the course of the reaction an initial portion of the tertiary amine which is normally liquid at ambient temperature in a quantity sufficient to produce free triazole for subsequent reaction without side reactions, said amine being substantially water-insoluble in free base form, but being water-soluble in salt form,
(d) adding the remainder of the required amount of the tertiary amine and the remainder of the required amount of the phenoxy compound to the reaction mixture, and
(e) upon termination of the reaction, washing the reaction mass with water under acid conditions to extract the tertiary amine salt into the water while leaving the desired product in the substantially tertiary amine-free organic solvent.

2. The process of claim 1 in which the initial amount of the phenoxy compound is mixed with about twice its molar amount of 1,2,4-triazole.

3. The process claim 2 in which the initial amount of the liquid tertiary amine is added in an amount which is approximately equal on a molar basis to the amount of the phenoxy compound.

4. The process of claim 1 in which the initial amount and the remainder of the phenoxy compound are approximately equal.

5. The process of claim 1 in which the remainder of the amine and of the phenoxy compound added in (d) are added alternately in at least two separate portions of amine and at least two separate portions of phenoxy compound.

6. The process of claim 1 which further includes the steps of (f) adding a base to the water containing tertiary amine salt to form a tertiary amine layer and an aqueous layer, (g) separating the tertiary amine layer, and (h) recycling the amine layer for preparation of a further quantity of the desired product.

7. The process of claim 1 in which X is chlorine.

8. The process of claim 1 in which n is 1 and X is chlorine.

9. The process of claim 1 in which the tertiary amine is a substantially water-insoluble substituted pyridine.

10. The process of claim 1 in which the tertiary amine is 2,4-dimethyl-pyridine.

11. The process of claim 1 in which the tertiary amine is represented by the formula $NR_1R_2R_3$ in which $R_1$, $R_2$ and $R_3$ each represents an alkyl group of up to 16 carbon atoms, an aralkyl group with up to 16 carbon atoms, or an aryl group having up to 16 carbon atoms.

12. The process of claim 11 in which $R_1$, $R_2$ and $R_3$ each represents an alkyl group of up to 4 carbon atoms or a benzyl group.

13. The process of claim 12 in which at least one of $R_1$, $R_2$ and $R_3$ represents a benzyl group.

14. The process of claim 1 in which the tertiary amine is N,N-dimethylbenzylamine.

15. The process of claim 1 in which the tertiary amine is added at an average rate of less than about 2% per minute.

16. The process of claim 1 in which the tertiary amine is added at a rate of less than about 1% per minute.

17. The process of claim 2 in which Y represents chlorine, n is 1, the tertiary amine is N,N-dimethylbenzylamine and N,N-dimethylbenzylamine is added at a rate of less than about 1% per minute.

18. The process of claim 1 in which the phenoxy compound is 4-(4-chlorophenoxy)-2,2-dimethyl-4-(1,2,4-triazol-1-yl)-butan-3-one of the formula.

* * * * *